(12) United States Patent  (10) Patent No.: US 8,771,387 B2
Simmons et al.  (45) Date of Patent: Jul. 8, 2014

(54) SYSTEMS AND METHODS FOR SOLAR-THERMAL GASIFICATION OF BIOMASS

(75) Inventors: Wayne Simmons, Dublin, OH (US); Christopher Perkins, Boulder, CO (US); Zoran Jovanovic, Lousiville, CO (US)

(73) Assignee: Sundrop Fuels, Inc., Longmont, CO (US)

( * ) Notice: Subject to any disclaimer, the term of this patent is extended or adjusted under 35 U.S.C. 154(b) by 904 days.

(21) Appl. No.: 12/796,045

(22) Filed: Jun. 8, 2010

(65) Prior Publication Data

US 2010/0237291 A1  Sep. 23, 2010

Related U.S. Application Data

(60) Provisional application No. 61/248,282, filed on Oct. 2, 2009, provisional application No. 61/185,492, filed on Jun. 9, 2009.

(51) Int. Cl.
   *B01J 7/00* (2006.01)

(52) U.S. Cl.
   USPC ............................................................. 48/61

(58) Field of Classification Search
   None
   See application file for complete search history.

(56) References Cited

U.S. PATENT DOCUMENTS

| 1,508,464 | A | 9/1924 | McFarland |
| 2,237,491 | A | 4/1941 | Kutz |
| 3,993,458 | A | 11/1976 | Antal, Jr. |
| 4,164,123 | A | 8/1979 | Smith |
| 4,219,492 | A | 8/1980 | Konoki et al. |
| 4,226,795 | A | 10/1980 | Bowman |
| 4,247,755 | A | 1/1981 | Smith, Jr. et al. |
| 4,290,779 | A | 9/1981 | Frosch et al. |
| 4,415,339 | A | 11/1983 | Aiman et al. |
| 4,455,153 | A | 6/1984 | Jakahi |
| 4,552,741 | A | 11/1985 | Melchoir |
| 4,582,590 | A | 4/1986 | Qader |

(Continued)

FOREIGN PATENT DOCUMENTS

| CN | 120405379 A | 4/2012 |
| CN | 102459528 A | 5/2012 |

(Continued)

OTHER PUBLICATIONS

International Preliminary Report on Patentability for International Application No. PCT/US10/37911, dated Dec. 12, 2011, 9 pages.

(Continued)

*Primary Examiner* — Imran Akram
(74) *Attorney, Agent, or Firm* — Rutan & Tucker, LLP

(57) ABSTRACT

A method, apparatus, and system for a solar-driven chemical plant that may include a solar thermal receiver having a cavity with an inner wall, where the solar thermal receiver is aligned to absorb concentrated solar energy from one or more of 1) an array of heliostats, 2) solar concentrating dishes, and 3) any combination of the two. Some embodiments may include a solar-driven chemical reactor having multiple reactor tubes located inside the cavity of solar thermal receiver, wherein a chemical reaction driven by radiant heat occurs in the multiple reactor tubes, and wherein particles of biomass are gasified in the presence of a steam ($H_2O$) carrier gas and methane ($CH_4$) in a simultaneous steam reformation and steam biomass gasification reaction to produce reaction products that include hydrogen and carbon monoxide gas using the solar thermal energy from the absorbed concentrated solar energy in the multiple reactor tubes.

15 Claims, 8 Drawing Sheets

(56) References Cited

U.S. PATENT DOCUMENTS

| | | | |
|---|---|---|---|
| 4,704,137 A | 11/1987 | Richter | |
| 4,756,722 A | 7/1988 | Knop et al. | |
| 4,766,154 A | 8/1988 | Bonnell et al. | |
| 4,881,947 A | 11/1989 | Parker et al. | |
| 5,154,597 A | 10/1992 | Fullemann et al. | |
| 5,179,129 A | 1/1993 | Studer | |
| 5,496,859 A | 3/1996 | Fong et al. | |
| 5,581,998 A | 12/1996 | Craig | |
| 5,618,500 A | 4/1997 | Wang | |
| 5,647,877 A | 7/1997 | Epstein | |
| 5,906,799 A | 5/1999 | Burgie et al. | |
| 6,402,988 B1 | 6/2002 | Gottzmann et al. | |
| 6,660,244 B2 | 12/2003 | Negishi et al. | |
| 6,676,716 B2 | 1/2004 | Fujimura et al. | |
| 6,872,378 B2 | 3/2005 | Weimer et al. | |
| 7,033,570 B2 | 4/2006 | Weimer et al. | |
| 7,207,327 B2 | 4/2007 | Litwin et al. | |
| 7,553,476 B2 | 6/2009 | Marrella et al. | |
| 7,632,476 B2 | 12/2009 | Shah et al. | |
| 7,686,856 B2 | 3/2010 | Hemmings et al. | |
| 7,856,829 B2 | 12/2010 | Shah et al. | |
| 7,871,457 B2 | 1/2011 | Shah et al. | |
| 7,881,825 B2 | 2/2011 | Esposito et al. | |
| 7,931,888 B2 | 4/2011 | Drnevich et al. | |
| 7,985,399 B2 | 7/2011 | Drnevich et al. | |
| 8,007,761 B2 | 8/2011 | Drnevich et al. | |
| 8,257,454 B1 | 9/2012 | Haueter et al. | |
| 8,378,151 B2 | 2/2013 | Perkins | |
| 2002/0134019 A1 | 9/2002 | Paisley | |
| 2003/0182861 A1 | 10/2003 | Weimer et al. | |
| 2003/0208959 A1 | 11/2003 | Weimer et al. | |
| 2003/0213514 A1 | 11/2003 | Ortabasi | |
| 2004/0170210 A1 | 9/2004 | Do et al. | |
| 2004/0219079 A1 | 11/2004 | Hagan et al. | |
| 2005/0020700 A1 | 1/2005 | Bahnisch | |
| 2005/0142049 A1 | 6/2005 | Amsden et al. | |
| 2005/0192362 A1 | 9/2005 | Rodriguez et al. | |
| 2006/0024538 A1 | 2/2006 | Steinberg | |
| 2006/0096298 A1 | 5/2006 | Barnicki et al. | |
| 2006/0140848 A1 | 6/2006 | Weimer et al. | |
| 2006/0188433 A1 | 8/2006 | Weimer et al. | |
| 2006/0225424 A1 | 10/2006 | Elliot et al. | |
| 2007/0098602 A1 | 5/2007 | Haueter et al. | |
| 2007/0129450 A1 | 6/2007 | Barnicki et al. | |
| 2007/0225382 A1 | 9/2007 | Van Den Berg et al. | |
| 2008/0022595 A1 | 1/2008 | Lemaire et al. | |
| 2008/0025884 A1 | 1/2008 | Tonkovich et al. | |
| 2008/0057366 A1 | 3/2008 | Katikaneni et al. | |
| 2008/0086945 A1 | 4/2008 | Wunning | |
| 2008/0086946 A1 | 4/2008 | Weimer et al. | |
| 2008/0104003 A1 | 5/2008 | Macharia et al. | |
| 2008/0209891 A1 | 9/2008 | Johannes et al. | |
| 2008/0222955 A1 | 9/2008 | Jancker et al. | |
| 2008/0223214 A1 | 9/2008 | Palamara et al. | |
| 2008/0284401 A1 | 11/2008 | Oettinger et al. | |
| 2008/0293132 A1 | 11/2008 | Goldman et al. | |
| 2008/0302670 A1 | 12/2008 | Boyle | |
| 2008/0307703 A1 | 12/2008 | Dietenberger et al. | |
| 2009/0013601 A1 | 1/2009 | Mandich et al. | |
| 2009/0014689 A1 | 1/2009 | Klepper et al. | |
| 2009/0018221 A1 | 1/2009 | Klepper et al. | |
| 2009/0018222 A1 | 1/2009 | Klepper et al. | |
| 2009/0018371 A1 | 1/2009 | Klepper et al. | |
| 2009/0018372 A1 | 1/2009 | Tirmizi et al. | |
| 2009/0064578 A1 | 3/2009 | Theegala | |
| 2009/0069452 A1 | 3/2009 | Robota | |
| 2009/0069609 A1 | 3/2009 | Kharas et al. | |
| 2009/0093555 A1 | 4/2009 | Stites et al. | |
| 2009/0151251 A1 | 6/2009 | Manzer et al. | |
| 2009/0151253 A1 | 6/2009 | Manzer et al. | |
| 2009/0156392 A1 | 6/2009 | Kharas | |
| 2009/0156393 A1 | 6/2009 | Kharas | |
| 2009/0156697 A1 | 6/2009 | Kharas | |
| 2009/0286295 A1 | 11/2009 | Medoff et al. | |
| 2009/0313886 A1 | 12/2009 | Hinman | |
| 2009/0318573 A1 | 12/2009 | Stites et al. | |
| 2010/0000874 A1 | 1/2010 | Hinman | |
| 2010/0022806 A1 | 1/2010 | Meitzner | |
| 2010/0075837 A1 | 3/2010 | Meitzner et al. | |
| 2010/0076228 A1 | 3/2010 | Alsum et al. | |
| 2010/0099925 A1 | 4/2010 | Kharas | |
| 2010/0099926 A1 | 4/2010 | Kharas | |
| 2010/0099927 A1 | 4/2010 | Kharas | |
| 2010/0137459 A1 | 6/2010 | Stites et al. | |
| 2010/0152497 A1 | 6/2010 | Stites | |
| 2010/0152498 A1 | 6/2010 | Kharas et al. | |
| 2010/0210741 A1 | 8/2010 | Kharas | |
| 2010/0212220 A1 | 8/2010 | Tirmizi | |
| 2010/0219062 A1 | 9/2010 | Leon Sanchez | |
| 2010/0237291 A1 | 9/2010 | Simmons | |
| 2010/0240780 A1 | 9/2010 | Holcombe | |
| 2010/0242352 A1 | 9/2010 | Perkins | |
| 2010/0242353 A1 | 9/2010 | Jovanovic | |
| 2010/0242354 A1 | 9/2010 | Perkins | |
| 2010/0243961 A1 | 9/2010 | Hilton | |
| 2010/0247387 A1 | 9/2010 | Perkins | |
| 2010/0249251 A1 | 9/2010 | Hilton | |
| 2010/0249468 A1 | 9/2010 | Perkins | |
| 2010/0270505 A1 | 10/2010 | Gallaspy et al. | |
| 2010/0273899 A1 | 10/2010 | Winter | |
| 2010/0280287 A1 | 11/2010 | Kharas et al. | |
| 2010/0282131 A1 | 11/2010 | Obrist et al. | |
| 2010/0303692 A1 | 12/2010 | Perkins | |
| 2010/0331581 A1 | 12/2010 | Kharas et al. | |
| 2011/0107661 A1 | 5/2011 | Tirmizi et al. | |
| 2011/0107662 A1 | 5/2011 | Tirmizi et al. | |
| 2011/0107663 A1 | 5/2011 | Tirmizi et al. | |
| 2011/0124927 A1 | 5/2011 | Stites et al. | |
| 2011/0155958 A1 | 6/2011 | Winter et al. | |
| 2011/0218254 A1 | 9/2011 | Chakravarti et al. | |
| 2011/0301732 A1 | 12/2011 | Gao et al. | |
| 2012/0145965 A1 | 6/2012 | Simmons et al. | |
| 2012/0181483 A1 | 7/2012 | Simmons | |
| 2012/0241677 A1 | 9/2012 | Perkins et al. | |

FOREIGN PATENT DOCUMENTS

| | | |
|---|---|---|
| JP | 2002/012877 A | 1/2002 |
| JP | 2002012877 | 1/2002 |
| SU | 1763814 A1 | 9/1992 |
| WO | WO 2010/144537 A1 | 12/2010 |
| WO | WO 2010/144537 A9 | 12/2010 |
| WO | WO 2010/144540 A1 | 12/2010 |
| WO | WO 2010/144542 A1 | 12/2010 |
| WO | WO 2010/144544 A1 | 12/2010 |
| WO | WO 2010/144547 A1 | 12/2010 |
| WO | WO 2010/144549 A1 | 12/2010 |
| WO | WO 2010/144552 A1 | 12/2010 |
| WO | WO 2010/144554 A1 | 12/2010 |
| WO | WO 2010/144556 A1 | 12/2010 |
| WO | WO 2011/139199 A1 | 10/2011 |
| WO | WO 2011/155962 A1 | 12/2011 |
| WO | WO 2013/148610 A1 | 3/2013 |
| WO | WO 2013/158343 A1 | 10/2013 |

OTHER PUBLICATIONS

International Preliminary Report on Patentability for International Application No. PCT/US10/37914, dated Dec. 12, 2011, 8 pages.
International Preliminary Report on Patentability for International Application No. PCT/US10/37923, dated Dec. 12, 2011, 13 pages.
International Preliminary Report on Patentability for International Application No. PCT/US10/37925, dated Dec. 12, 2011, 10 pages.
International Preliminary Report on Patentability for International Application No. PCT/US10/37930, dated Dec. 12, 2011, 13 pages.
International Preliminary Report on Patentability for International Application No. PCT/US10/37934, dated Dec. 12, 2011, 10 pages.
International Preliminary Report on Patentability for International Application No. PCT/US10/37938, dated Dec. 12, 2011, 10 pages.
International Preliminary Report on Patentability for International Application No. PCT/US10/37940, dated Dec. 12, 2011, 10 pages.
International Preliminary Report on Patentability for International Application No. PCT/US10/37944, dated Dec. 12, 2011, 10 pages.

(56) References Cited

OTHER PUBLICATIONS

Cross Reference to Related Applications Under 27 C.F.R. 1.78, 2 pages.
International Search Report for PCT/US10/037911, dated Aug. 6, 2010, 2 pages.
International Search Report for PCT/US10/037914, dated Aug. 13, 2010, 2 pages.
International Search Report for PCT/US10/037923, dated Aug. 9, 2010, 3 pages.
International Search Report for PCT/US10/037925, dated Aug. 10, 2010, 3 pages.
International Search Report for PCT/US10/037930, dated Sep. 20, 2010, 5 pages.
International Search Report for PCT/US10/037934, dated Aug. 9, 2010, 2 pages.
International Search Report for PCT/US10/037938, dated Aug. 5, 2010, 2 pages.
International Search Report for PCT/US10/037940, dated Aug. 13, 2010, 2 pages.
International Search Report for PCT/US10/037944, dated Aug. 18, 2010, 2 pages.
Munzinger, M., et al., "Biomass Gass ification Using Solar Thermal Energy", *Anzses 2006*, pp. 1-10.
Mishra, Anuradha, et al., "Thermal Optimization of Solar Biomass Hybrid Cogeneration Plants", *Journal of Scientific & Industrial Research*, vol. 65, Apr. 2006, pp. 355-363.
Esser, Peter, et al., "The Photochemical Synthesis of Fine Chemicals With Sunlight," Angew. Chem. Int. Ed. Engl. 1994, vol. 33, pp. 2009-2023.
Notice of Allowance for U.S. Appl. No. 12/796,121 mailed Oct. 11, 2012, 7 pages. U.S. Patent and Trademark Office, Alexandria, Virginia USA.
Non-Final Office Action for U.S. Appl. No. 12/796,121 mailed Jun. 7, 2012, 10 pages. U.S. Patent and Trademark Office, Alexandria, Virginia USA.
Non-Final Office Action for U.S. Appl. No. 12/796,222 mailed Jan. 29, 2013, 48 pages. U.S. Patent and Trademark Office, Alexandria, Virginia USA.
Restriction Requirement for U.S. Appl. No. 12/796,319 mailed Jun. 20, 2013, 5 pages. U.S. Patent and Trademark Office, Alexandria, Virginia USA.
Restriction Requirement for U.S. Appl. No. 12/796,428 mailed Oct. 9, 2012, 7 pages. U.S. Patent and Trademark Office, Alexandria, Virginia USA.
Non-Final Office Action for U.S. Appl. No. 12/796,471 mailed May 3, 2013, 22 pages. U.S. Patent and Trademark Office, Alexandria, Virginia USA.
Restriction Requirement for U.S. Appl. No. 12/796,471 mailed Mar. 13, 2013, 6 pages. U.S. Patent and Trademark Office, Alexandria, Virginia USA.
Restriction Requirement for U.S. Appl. No. 12/795,910 mailed Feb. 20, 2013, 6 pages. U.S. Patent and Trademark Office, Alexandria, Virginia USA.
Non-Final Office Action for U.S. Appl. No. 12/795,947 mailed Mar. 14, 2013, 28 pages. U.S. Patent and Trademark Office, Alexandria, Virginia USA.
Restriction Requirement for U.S. Appl. No. 12/795,947 mailed Oct. 9, 2013, 5 pages. U.S. Patent and Trademark Office, Alexandria, Virginia USA.
Final Office Action for U.S. Appl. No. 12/795,989 mailed Jul. 16, 2013, 28 pages. U.S. Patent and Trademark Office, Alexandria, Virginia USA.
Non-Final Office Action for U.S. Appl. No. 12/795,989 mailed Jan. 24, 2013, 29 pages. U.S. Patent and Trademark Office, Alexandria, Virginia USA.
Written Opinion for International Application No. PCT/US2010/037923 mailed Aug. 9, 2010, 11 pages.
Written Opinion for International Application No. PCT/US2010/037911 mailed Aug. 6, 2010, 7 pages.
Written Opinion for International Application No. PCT/US2010/037914 mailed Aug. 13, 2010, 6 pages.
Written Opinion for International Application No. PCT/US2010/037925 mailed Aug. 10, 2010, 8 pages.
Written Opinion for International Application No. PCT/US2010/037930 mailed Sep. 20, 2010, 11 pages.
Written Opinion for International Application No. PCT/US2010/037934 mailed Aug. 9, 2010, 8 pages.
Written Opinion for International Application No. PCT/US2010/037940 mailed Aug. 13, 2010, 8 pages.
Written Opinion for International Application No. PCT/US2010/037944 mailed Aug. 18, 2010, 8 pages.
*Netscape Communications Corp, v. ValueClick, Inc.*, 684 F. Supp. 2d. 678—Dist. Court, ED Virginia 2010. No. 1:09cv225. United States District Court, E.D. Virginia, Alexandria Division. Oct. 22, 2009. 38 pages.
*Ex Parte Wada and Murphy*, U.S. Patent and Trademark Office Board of Patent Appeals and Interferences Decision on Appeal dated Jan. 14, 2008, 9 pages.
*Ex Parte Chapman*, U.S. Patent and Trademark Office Board of Patent Appeals and Interferences Decision on Appeal dated Feb. 9, 2012 for Appeal No. 2009-010238, U.S. Appl. No. 10/751,616, 6 pages.
Office Action for Chinese Patent Application No. 2010800025964.1 mailed Sep. 4, 2013, 30 pages. State Intellectual Property Office of PRC.
Restriction Requirement for U.S. Appl. No. 12/795,947 mailed Oct. 9, 2012, 5 pages. U.S. Patent and Trademark Office, Alexandria, Virginia, USA.
Final Office Action for U.S. Appl. No. 12/796,222 mailed Jun. 8, 2010, 34 pages. U.S. Patent and Trademark Office, Alexandria, Virginia, USA.
Bridgwater, et al., "Fast Pyrolysis Processes for Biomass," Renewable and Sustainable Energy Reviews, vol. 4, No. 1, 73 pages, Mar. 2000.
Lede, "Solar Thermochemical Conversion of Biomass", Solar Energy, vol. 65, No. 1, 11 pages, Jan. 1, 1999.
Decision on Petition for the U.S. Appl. No. 12/795,910 mailed Jun. 22, 2010, 2 pages. U.S. Patent & Trademark Office, Alexandria, Virginia USA.
Non-Final Office Action for U.S. Appl. No. 13/254,020 mailed May 9, 2013, 20 pages. U.S. Patent & Trademark Office, Alexandria, Virginia USA.
International Search Report and Written Opinion for International Patent Application No. PCT/US10/59564, dated Mar. 2, 2011, 11 pages. International Searching Authority/US Alexandria, Virginia, USA.
Notification Concerning Transmittal of International Preliminary Report on Patentability for International Patent Application No. PCT/US2010/059564, dated Dec. 20, 2012, 10 pages. The International Bureau of WIPO, Geneva, Switzerland.
International Search Report and Written Opinion, International Patent Application No. PCT/US2013/033773, dated Jun. 18, 2013, 14 pages. International Searching Authority/US, Alexandria, Virginia, USA.
Restriction Action for U.S. Patent & Trademark Office, U.S. Appl. No. 13/254,020 mailed Nov. 26, 2012, 6 pages. U.S. Patent & Trademark Office, Alexandria, Virginia USA.
Office Action for Chinese Patent Application No. 201080017429.1 mailed Aug. 2, 2013, 10 pages, State Intellectual Property Office of PRC.
Non-Final Office Action for U.S. Appl. No. 12/796,222 mailed Oct. 30, 2013, 6 pages. U.S. Patent and Trademark Office, Alexandria, Virginia, USA.
Final Office Action for U.S. Appl. No. 12/796,471 mailed Nov. 27, 2013, 20 pages. U.S. Patent and Trademark Office, Alexandria, Virginia, USA.
Non-Final Office Action for U.S. Appl. No. 12/795,910 mailed Sep. 12, 2013, 7 pages. U.S. Patent & Trademark Office, Alexandria, Virginia USA.
Higuchi, Takayoshi "Steam Explosion of Wood", Sections 1-4, Biomass Handbook, © 1989 by OPA (Amsterdam), pp. 470-473 plus Cover, Biblio, Table of Contents excerpt. 7 pages total, Editors:

(56) References Cited

OTHER PUBLICATIONS

Osamu Kitani & Carl W. Hall, ISBN 2-88124-269-3, Gordon and Breach Science Publishers S. A., Cooper Station, New York, New York.
"StakeTech—First Pulping System Receives Full Acceptance", May 14, 1996, 2 pages. Publisher: Business Wire. downloaded from http://www.thefreelibrary.com/StakeTech.
McCallum, Don, "Medium Density Fiber Board" pp. 8-11, Nov. 1, 1996 http://fennerschool-associated.anu.edu.au/fpt/mdf/manufacture.html.
Office Action for Chinese Patent Application No. 201080024924.5 mailed Jul. 10, 2013, 7 pages, State Intellectual Property Office of PRC.
Restriction Requirement for U.S. Appl. No. 13/429,794 mailed May 24, 2013, 5 pages. U.S. Patent and Trademark Office, Alexandria, Virginia USA.
Final Office Action for U.S. Appl. No. 12/795,947 mailed Oct. 2, 2013, 22pgs. U.S. Patent and Trademark Office, Alexandria, Virginia, USA.
Advisory Action for U.S. Appl. No. 12/795,947 mailed Jan. 21, 2014, 3 pgs. U.S. Patent and Trademark Office, Alexandria, Virginia, USA.
Office Action for Chinese Patent Application No. 201080025216.3 mailed Jun. 20, 2013, 7 pages, State Intellectual Property Office of PRC.
Restriction Requirement for U.S. Appl. No. 13/254,020 mailed Nov. 26, 2012, 5 pages. U.S. Patent and Trademark Office, Alexandria, Virginia USA.
Non-Final Office Action for U.S. Appl. No. 13/254,020 mailed May 9, 2013, 20 pages. U.S. Patent and Trademark Office, Alexandria, Virginia, USA.
Notification of Transmittal of the International Search Report and the Written Opinion of the International Searching Authority for International Application No. PCT/US2010/037940 mailed Aug. 13, 2010, 11 pages. International Searching Authority/US, Alexandria, Virginia USA.
Notification Concerning Transmittal of International Preliminary Report on Patentability for International Application No. PCT/US2010/037940 mailed Dec. 12, 2011, 10 pages. International Bureau of WIPO, Geneva, Switzerland.
Notification of Transmittal of the International Search Report and the Written Opinion of the International Searching Authority for International Application No. PCT/US10/059564 mailed Mar. 2, 2011 11 pages. International Searching Authority/US, Alexandria, Virginia USA.
Non-Final Office Action for U.S. Appl. No. 13/429,794 mailed Nov. 1, 2013, 7 pages. U.S. Patent and Trademark Office, Alexandria, Virginia, USA.
Final Office Action for U.S. Appl. No. 13/254,020 mailed Oct. 29, 2013, 21pgs. U.S. Patent and Trademark Office, Alexandria, Virginia, USA.
International Search Report and Written Opinion for International Application No. PCT/US2013/033920 mailed Jun. 14, 2013, 15 pages. International Searching Authority/US, Alexandria Virginia USA.
Notice of Allowance for U.S. Appl. No. 12/796,319 mailed Dec. 9, 2013, 12 pages. U.S. Patent and Trademark Office, Alexandria, Virginia, USA.
Non-Final Office Action for U.S. Appl. No. 12/796,222 mailed Jan. 29, 2013, 44 pages. U.S. Patent & Trademark Office, Alexandria, Virginia USA.
Non-Final Office Action for U.S. Appl. No. 12/796,222 mailed Jan. 8, 2014, 35 pages. U.S. Patent & Trademark Office, Alexandria, Virginia USA.

Multiple tube reactor

(Biomass Methane)

Feed Composition

| Biomass | wt% |
|---|---|
| Cellulose | 69.09 |
| Lignin | 22.02 |
| Ash | 8.89 |

Reactions $C_6H_{10}O_5$ (cellulose) + $H_2O$ → $6\,CO + 6\,H_2$ $C_{10}H_{12}O_3$ (lignin) + $7\,H_2O$ → $10\,CO + 13\,H_2$ $CH_4 + H_2O$ → $CO + 3\,H_2$

Material & Energy Balance (T = 1200°C)

| | | | | Energy | | HHV | |
|---|---|---|---|---|---|---|---|
| | kmol/day | HHV (J/mol) | J/day | GWhr/day | GWhr/yr | | |
| Cellulose | 854.08 | 2.83E+06 | 2.41E+12 | 0.67 | 244.68 | Reactants | |
| Lignin | 245.04 | 3.82E+06 | 9.35E+11 | 0.26 | 94.82 | | |
| CH4 | 6837.92 | 8.90E+05 | 6.09E+12 | 1.69 | 617.29 | 956.78 | GWhr/yr |
| H2 | 28823.76 | 2.85E+05 | 8.23E+12 | 2.29 | 834.20 | H2, CO Products | |
| CO | 14412.8 | 3.05E+05 | 4.40E+12 | 1.22 | 446.15 | 1280.35 | GWhr/yr |

$Q_R$ = 579 GWhr/yr        HHV Products/HHV Reactants = 1.34

FIG. 4

SYSTEMS AND METHODS FOR SOLAR-THERMAL GASIFICATION OF BIOMASS

RELATED APPLICATIONS

This application claims the benefit of both U.S. Provisional Patent Application Ser. No. 61/248,282, filed Oct. 2, 2009 and entitled "Various Methods and Apparatuses for Sun Driven Processes," and U.S. Provisional Patent Application Ser. No. 61/185,492, titled "VARIOUS METHODS AND APPARATUSES FOR SOLAR-THERMAL GASIFICATION OF BIOMASS TO PRODUCE SYNTHESIS GAS" filed Jun. 9, 2009, both of which are hereby incorporated herein by reference in their entireties.

NOTICE OF COPYRIGHT

A portion of the disclosure of this patent document contains material that is subject to copyright protection. The copyright owner has no objection to the facsimile reproduction by anyone of the software engine and its modules, as it appears in the Patent and Trademark Office Patent file or records, but otherwise reserves all copyright rights whatsoever.

FIELD OF THE INVENTION

Embodiments of the invention generally relate to systems, methods, and apparatus for refining biomass and other materials. More particularly, an aspect of an embodiment of the invention relates to solar-driven systems, methods, and apparatus for refining biomass and other materials.

BACKGROUND OF THE INVENTION

Biomass gasification is an endothermic process; energy must be put into the process to drive it forward. Typically, this is performed by partially oxidizing (burning) the biomass itself. Between 30% and 40% of the biomass must be consumed to drive the process, and at the temperatures which the process is generally limited to (for efficiency reasons), conversion is typically limited, giving still lower yields. In contrast, the proposed solar-driven biorefinery uses an external source of energy (solar) to provide the energy required for reaction, so none of the biomass need be consumed to achieve the conversion. This can result in significantly higher yields of gallons of gasoline per biomass ton than previous technologies, as the energy source being used to drive the conversion is renewable and carbon free. In addition, chemical reactors are generally engineered to operate at constant conditions around the clock.

SUMMARY OF THE INVENTION

Some embodiments relate to a solar-driven chemical plant, including a solar thermal receiver having a cavity with an inner wall, where the solar thermal receiver can be aligned to absorb concentrated solar energy from one or more of 1) an array of heliostats, 2) solar concentrating dishes, and 3) any combination of the two.

In some embodiments, a solar-driven chemical reactor having multiple reactor tubes is located inside the cavity of a solar thermal receiver. A chemical reaction driven by radiant heat occurs in the multiple reactor tubes. Particles of biomass may be gasified in the presence of a steam ($H_2O$) carrier gas and methane ($CH_4$) in a simultaneous steam reformation and steam biomass gasification reaction to produce reaction products that include hydrogen and carbon monoxide gas using the solar thermal energy from the absorbed concentrated solar energy in the multiple reactor tubes.

In some embodiments, a solar-driven reactor may be located inside a receiver, which is a cavity that transforms solar radiant energy into thermal energy. The receiver can include multiple reactor tubes that allow methane or natural gas and steam to pass through a fluidized bed of inert particles to cause a steam methane reaction. When natural gas is passed through a stream methane reaction occurs with a dry reforming of methane with $CO_2$ occurs. Additionally, multiple reactors may be incorporated in the receiver.

BRIEF DESCRIPTION OF THE DRAWINGS

The drawings refer to embodiments of the invention in which:

FIG. 4 illustrates results from simulations of the solar-thermal gasification of biomass with methane;

Figure 1:
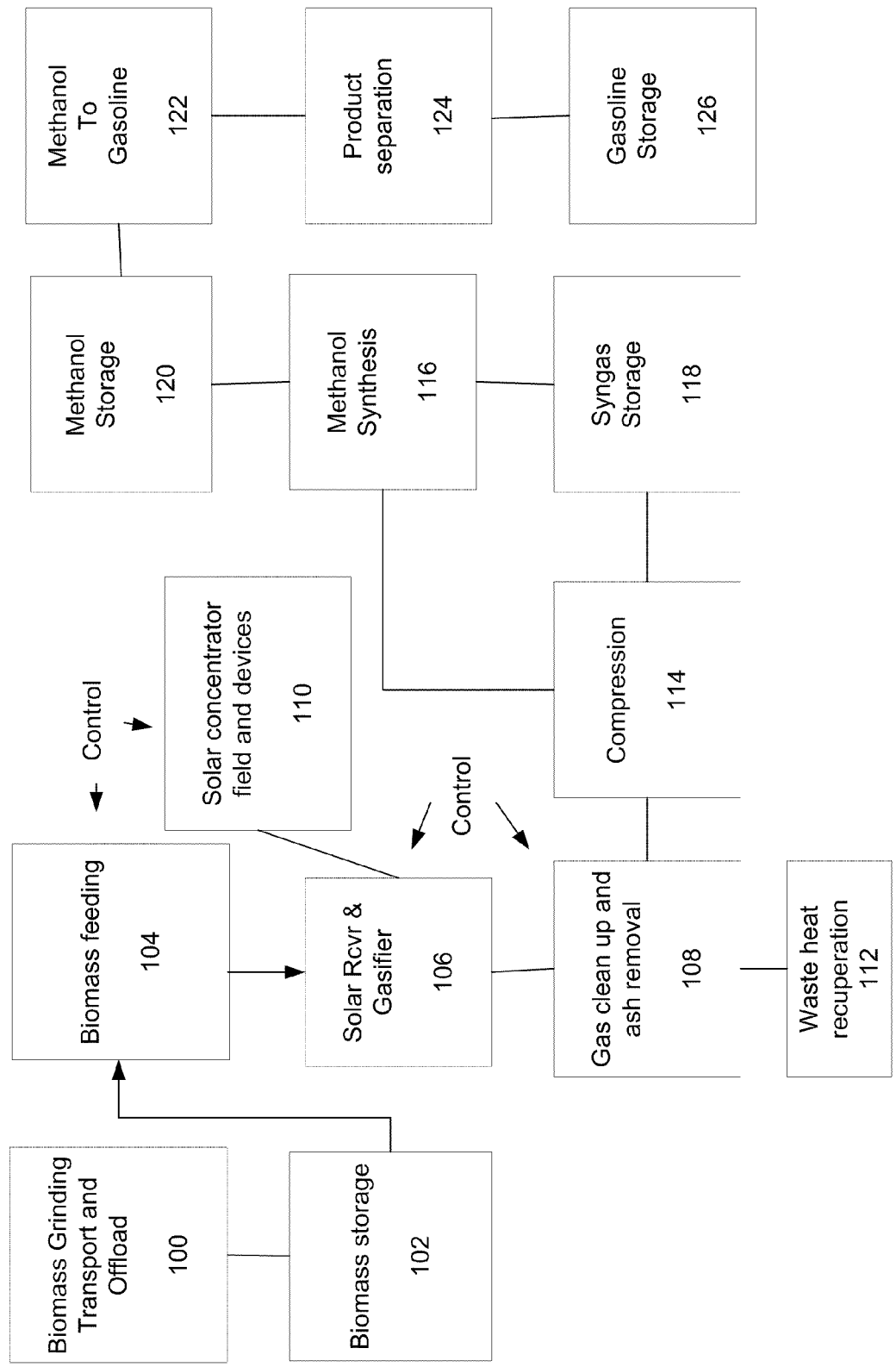
FIG. 1 illustrates a block diagram of an embodiment of an example process flow in accordance with the systems and methods described herein.

While the invention is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the invention.

DETAILED DISCUSSION

In the following description, numerous specific details are set forth, such as examples of specific data signals, named components, connections, number of reactor tubes, etc., in order to provide a thorough understanding of the present invention. It will be apparent, however, to one of ordinary skill in the art that the present invention may be practiced without these specific details. In other instances, well known components or methods have not been described in detail but rather in a block diagram in order to avoid unnecessarily obscuring the present invention. Further, specific numeric references such as first reactor tube, may be made. However, the specific numeric reference should not be interpreted as a literal sequential order but rather interpreted that the first reactor tube is different from a second reactor tube. Thus, the specific details set forth are merely exemplary. The specific details may be varied from and still be contemplated to be within the spirit and scope of the present invention. The term coupled is defined as meaning connected either directly to the component or indirectly to the component through another component.

In some embodiments, a solar-driven chemical reactor may have multiple reactor tubes located inside the cavity of a solar thermal receiver. Within the cavity, a chemical reaction can be driven by radiant heat. The reaction may occur in the multiple reactor tubes. Additionally, particles of biomass can be gasified in the presence of a steam (H2O) carrier gas and methane (CH4) in a simultaneous steam reformation and steam biomass gasification reaction. This can produce reaction products that include hydrogen and carbon monoxide gas using the solar thermal energy from the absorbed concentrated solar energy in the multiple reactor tubes.

In some embodiments, a solar-driven reactor is located inside a receiver, which is a cavity that transforms solar radiant energy into thermal energy. The receiver can include multiple reactor tubes allowing methane or natural gas and steam to pass through a fluidized bed of inert particles to cause a steam methane reaction. When natural gas is passed through a stream, a methane reaction occurs with a dry reforming of methane with CO2 occurs.

FIG. 1 illustrates a block diagram of an example process flow in accordance with the systems and methods described herein. Some embodiments encompass a solar-driven-biomass gasification to a liquid fuel/electrical process. The process might also include generation, chemical processing, or biochar, for solar generated syngas derivative products or other similar technical process. In a specific example implementation the process described is a solar-driven-biomass gasification to 'green' liquid fuel process. In an embodiment, this process includes one or more of the following process steps.

Biomass grinding or densification, transport and offload 100 may be part of the overall process. Bales of the biomass can be compressed and densified by a compactor to facilitate transport to on-site via the densification achieved by the double compression. The bales are sized to dimensions that may, for example, fit within a standard box car size or fit within standard compactor size. The entrained-flow biomass feed system can be preceded by a grinding system equipped with mechanical cutting device and a particle classifier, such as a perforated screen or a cyclone, to control the size of the particles that are. The grinding system that has a mechanical cutting device such as a screw and set of filters with micron sized holes/screen diameter sized holes to control particle size. The mechanical screw and set of filters cooperate to grind and pulverize the stock biomass to particles to the micron sized holes of the filters, and the particles of biomass are then fed into and gasified in the solar-driven chemical reactor. The biomass may be in an embodiment non-food stock biomass. In other cases, food stock biomass or a combination of the two might also be processed.

The biomass may be stored 102. As needed, the biomass might be feed 104 into an example system or apparatus of the instant application. For example, after grinding and pulverizing the biomass to particles, the particles of biomass can be fed into and gasified in the solar-driven chemical reactor. Two or more feed line supply the particles of biomass having an average smallest dimension size between 50 microns (um) and 2000 um to the chemical reactor. An entrained gas biomass feed system uses an entrainment carrier gas to move a variety of biomass sources fed as particles into the solar driven chemical reactor.

A solar receiver and gasifier 106 may be used to break down the biomass. An example biomass gasifier design and operation can include a solar chemical reactor and solar receiver to generate components of syngas.

Quenching, gas clean up, and ash removal 108 from biomass gasifier 106 may be provided for. Some non-pilot syngas may exit the system 112. Some gasses may be a waste product, while other gasses can be compressed 114 prior to storage 118 or e.g., methanol synthesis 116. Methanol may then be stored 120 for later methanol to gasoline conversion 122.

An on-site fuel synthesis reactor that is geographically located on the same site as the chemical reactor and integrated to receive the hydrogen and carbon monoxide products from the gasification reaction can be used in some embodiments. Additionally, the on-site fuel synthesis reactor has an input to receive the hydrogen and carbon monoxide products and use them in a hydrocarbon fuel synthesis process to create a liquid hydrocarbon fuel. The on-site fuel synthesis reactor may be connected to the rest of the plant facility by a pipeline that is generally less than 15 miles in distance. The on-site fuel synthesis reactor may supply various feedback parameters and other request to the control system. For example, the on-site fuel synthesis reactor can request the control system to alter the H2 to CO ratio of the syngas coming out of the quenching and gas clean up portion of the plant and the control system will do so.

In various embodiments, synthesis gas may be fed to another technical application. Examples include a syngas to other chemical conversion process. The other chemical or chemicals produced can include liquefied fuels such as transportation liquefied fuels. In an example hydrocarbon based fuel, methanol 116 may be formed from syngas. The methanol may be further converted to gasoline or other fuels 122 and various products may be separated out from the gasoline 124 or syngas. These products, e.g., gasoline, may then be stored for later use as an energy source.

As noted, these biomass feedstock resources can include energy crops such as miscanthus and switchgrass, which are high-impact and high-yield energy crops. A biomass with low lignin content will make it easier to gasify and process in the solar gasifier.

The stock biomass, such as rice straw, rice hulls, corn stover, high biomass sorghum, switchgrass, miscanthus, bales can be double compressed to facilitate transport via the densification achieved by the double compression allowing very high loadings on the train cars.

Some embodiments use steam reforming of natural gas, sometimes referred to as steam methane reforming (SMR). SMR is a method to produce hydrogen and carbon monoxide for syngas. At high temperatures (700-1500° C.) and in the presence of, for example, a metal-based catalyst (nickel), steam reacts with methane to yield carbon monoxide and hydrogen. In some examples, natural gas may be a mixture of methane and other gases found in deposits under the earth and may contain small amounts of CO2.

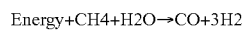

$$\text{Energy} + CH_4 + H_2O \rightarrow CO + 3H_2$$

Additional hydrogen can be recovered by a lower-temperature gas-shift reaction with the carbon monoxide produced. The reaction is summarized by: $CO + H_2O \rightarrow CO_2 + H_2$. However, sometimes it is beneficial to eliminate this water gas shift reaction in order to reduce the amount of CO2 present in the generated synthesis gas. The elimination of the water gas shift reaction may be accomplished by a rapid quenching of the generated products from the reactor at an exit temperature of greater than 900 centigrade to 400 degree or less within 10 seconds.

In some embodiments, carbon dioxide reforming (also known as dry reforming of methane with CO2) is a method of producing synthesis gas (mixtures of hydrogen and carbon monoxide) from the reaction of carbon dioxide with hydrocarbons such as methane.

The methane carbon dioxide reforming reaction may be represented by: CO2+CH4→2H2+2CO In some embodiments using biomass gasification, the carbonaceous biomass material particles are fed from the entrained flow biomass feed system. The particles can undergo several distinct chemical processes of the gasification reaction prior to exiting the reactor tubes including the following. For example, initially, pyrolysis of the carbonaceous biomass particles can produce carbonaceous char and volatile components vaporized into gas products.

In some embodiments, complete gasification of the carbonaceous char including lignin fractions produce gaseous products including carbon monoxide, hydrogen, and tars as well as greater than 99% pure carbonaceous ash. Additionally, cracking of the tars, including larger hydrocarbons and aromatic compounds collectively known as tars, may occur at greater than 1000 degrees C. to produce the substantial tar destruction to less than below 50 mg/m^3 and complete gasification of greater than 90% of the biomass particles into reaction products including hydrogen and carbon monoxide gas.

The steps of at least the complete gasification and cracking of tars starts and finishes within the residence time of the biomass particles in the reaction zone in the chemical reactor between the range of 0.01 and 5 seconds. The pyrolysis may start with a low temperature of 300 degree C. or less preheating by the carrier gas prior to entering the reactor tubes.

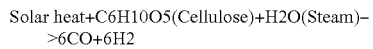

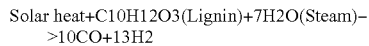

This thermochemical process allows conversion of the entire biomass feedstock (cellulose, hemi-cellulose, and lignin), thereby reducing the amount of ash present in reaction products and producing a flexible synthesis gas. At least two of the above reactions occur in some embodiments and generally in an embodiment all three reactions occur simultaneously in the reactor tubes.

Some embodiments may use a fixed bed of carbonaceous fuel (e.g. biomass) through which the gasification agent, e.g., steam, oxygen, air, and/or any combination, flows in a co-current configuration with the fuel downwards. Additionally, a steam blown fluidized bed gasifier may be used to produce a CO2 free gas with a high energy value. Alternatively, small particles of the biomass may be entrained in the gas streams of natural gas and/or gasification agent to mix in the biomass gasification process. Either way, the gasification zone may have steam, biomass, and potentially a methane type reactant which generates biomass gasification reactions as described herein.

The receiver generally encloses multiple reactor tubes. In an embodiment, the reactor tubes allow methane or natural gas and steam to pass through a heat transfer aid to cause a solar driven steam methane reaction to occur. The heat transfer aid is used to heat the reactant gases. The heat transfer aid may be one or more of the following located inside each reactor tube: a fluidized bed of inert particles, reticulate porous ceramic (RPC) foam, a ceramic monolith, ceramic tubes or aerogels, open structured packed rings such as Raschig rings, or gauze or wire constructed of a high temperature-resistant material. Radiation is the primary mode of heat transfer to the heat transfer aids from the reactor tube walls, and conduction, convection, or some combination of the two are secondary modes of heat transfer.

Some embodiments may add methane to the biomass. When compared to systems that do not add methane may include the following:

(1) The energy requirement of the solar reactor to produce the equivalent amount of syngas is 33% lower, thus lowering the cost of solar capital components. The energy released in going from 1:1 H2:CO syngas to a H2:CO 2:1 syngas may be contained in the gas stream (as sensible energy). Practically, it can take more solar energy in a pure biomass gasification case to get to the same amount of syngas, but only because you can't practically get the sensible heat back into the feed stream before gasification; and (2) The above results confirm that various biomass sources ("Kentucky Bluegrass," lignin, corn stover, sorghum) can be gasified at high temperature within seconds using a solar-heated transport tube reactor and that tar formation can be substantially reduced or eliminated.

Figure 2:
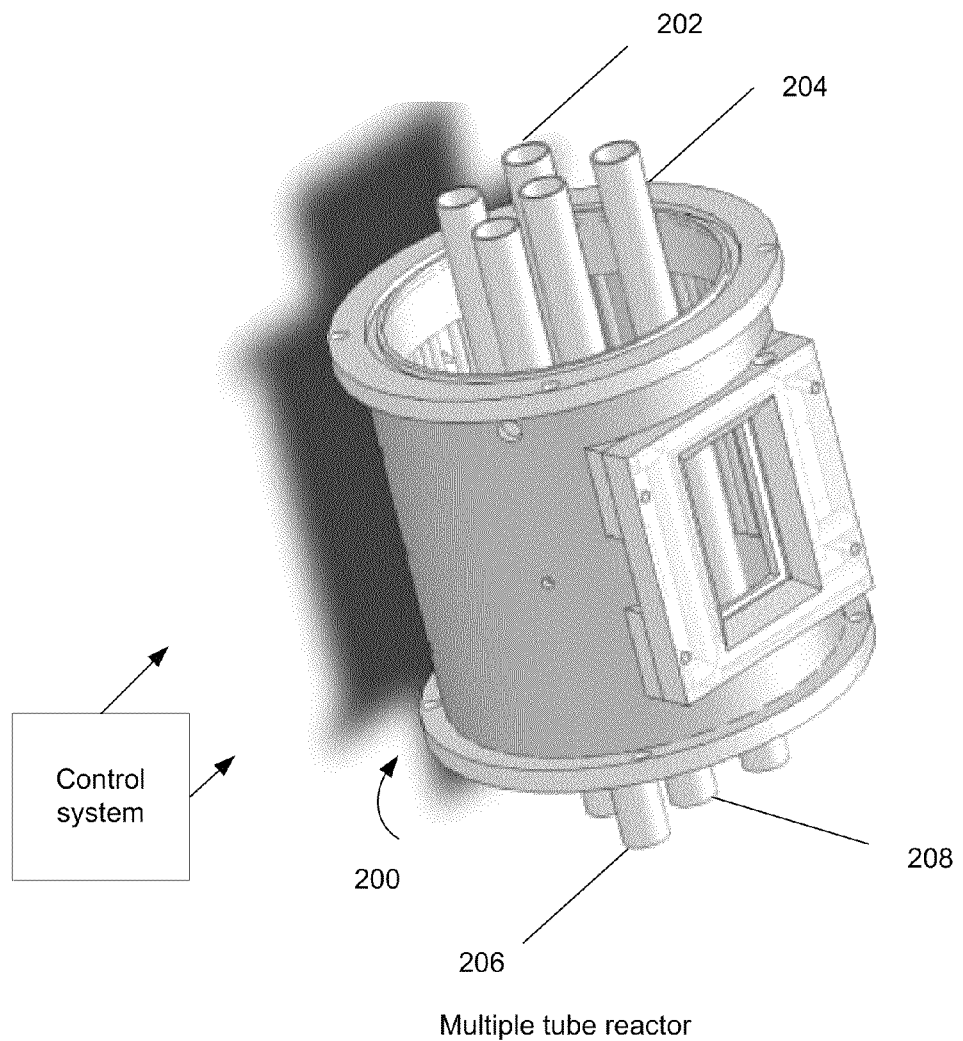
FIG. 2 illustrates a diagram of an embodiment of an example multiple tube reactor in accordance with the systems and methods described herein.

FIG. 2 illustrates a diagram of an example multiple tube chemical reactor 200 that may be used in a solar driven system. Reactor 200 has multiple reactor tubes 202, 204, 206, 208 and a separate entrainment line may be used for each of the gasifier reactor tubes 202, 204, 206, 208 in the chemical reactor 200. This may allow for independent temperature control and balancing of the amount of particles of biomass flowing in each of the reactor tubes 202, 204, 206, 208 in the multiple tube solar driven chemical reactor 200. The particles of biomass feed can be distributed to the reactor tubes 202, 204, 206, 208 by a lock hopper rotary feed system, such as a Rotofeed® lock hopper rotary feed system. Such a system can allow for balanced feeding to individual reactor tubes 202, 204, 206, 208 and feed rate of the particles is controlled by a weight measuring metering device such as load cells. It may also allow for controlling the rotational rate of the screw or auger that can move set amounts of biomass along the axis of rotation of the auger. The auger may be located at the base of the lock hopper and can be controlled by a computerized control system such as a Programmable Logic Controller, PC, MAC, CNC, etc, to respond to feed demands of the system. In an embodiment, the computerized control system controls the feed rate of particles of stock biomass in the solar driven chemical reactor based on an amount of solar energy available indicated by sensors including temperature sensors and/or light meters.

A solar-driven bio-refinery can include a solar driven chemical reactor that has a cyclic operation rather than a continuous steady state operation. Additionally, a computerized control system with sensors may control the feed rate of the biomass material into the multiple reactor tubes with well controlled feed rates that can respond by changing the feed rate of the biomass material based on changing solar availability.

In some embodiments, a solar-driven chemical reactor can have multiple reactor tubes located inside the cavity of a solar thermal receiver. A chemical reaction can be driven by radiant heat. The reaction can occur in the multiple reactor tubes such that particles of biomass are gasified in the presence of a steam (H2O) carrier gas and methane (CH4). This may occur in a simultaneous steam reformation and steam biomass gasification reaction to produce reaction products that include hydrogen and carbon monoxide gas using the solar thermal energy from the absorbed concentrated solar energy in the multiple reactor tubes.

In some embodiments, the solar-thermal chemical reactor converts carbonaceous biomass materials into carbon monoxide and hydrogen by reacting the raw particles of biomass material with the steam (biomass gasification) and the steam. For example, this may occur with the supplemental methane steam reforming at high temperatures, 700-1500 C, with a controlled amount of steam, oxygen, air, and/or any combination, which results in the gas mixture of synthesis gas. Additionally, the steam reacts with both the biomass and the methane, but biomass and methane do not react with each other. A lower amount of steam ($H_2O$) to carbon ratio can be better. In some embodiments, the ratio can be 1:1 to 1:4.

Additionally, a steam reforming process at a high temperature of 700-1500° C. may provide a reaction that avoids a water gas shift reaction that occurs at lower temperatures. This can avoid $CO_2$ creation and still provide a 2:1 $H_2$:CO ratio. For example, a reaction using methane with a steam reforming reaction may allow the reaction in the reactor to generate the correct molar ratio without a water-gas-shift reaction.

In some embodiments, $CO_2$ may generally be formed in the reaction product gas stream as a result of the water-gas-shift reaction occurring, especially with water feed, and the WGS could be used to achieve a desired molar ratio of $H_2$:CO=2. However, by material balancing the steam reforming of the natural gas the desired molar ratio of $H_2$:CO=2 can be achieved without the secondary WGS, which would also generate $CO_2$.

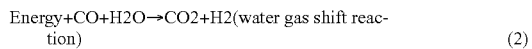

$$\text{Energy} + CO + H_2O \rightarrow CO_2 + H_2 \text{(water gas shift reaction)} \quad (2)$$

wherein the steam reforming reaction is generating a 3:1 $H_2$:CO ratio and the biomass is generating a 1:1 ratio so less biomass is needed to achieve a 2:1 ratio. In some examples, less energy is needed because all of these reactions are endothermic being driven simultaneously by the concentrated solar energy.

As illustrated in FIG. 2, a control system may be used to balance the biomass gasification reaction, stream reforming reaction, and dry reforming reaction. For example, balancing gasification with the amount of concentrated solar energy available directed at the solar thermal receiver and solar chemical reactor to keep a temperature at which the chemical reactor operates high enough to maintain the molar ratio of $H_2$ to CO ratio.

In some embodiments, a control system may be used to keep a reaction temperature high enough for substantially an entire conversion of biomass to product gases and elimination of tar products. For example, the temperature might be at least 1100-1300 degree C. This may provide a reaction that has less than 200 mg/m^3 while keeping the temperature low enough such that the reactor tube wall temperature can be less than 1600 degrees C. so that the walls are not structurally weakened. Such temperatures may also significantly reduce receiver efficiency. Additionally, the control system may control the amount of $H_2O$, natural gas, and biomass particles to keep the generated syngas within the desired $H_2$:CO ratio while the chemical reaction can be substantially tar free and have less than 7% by volume CO in the generated syngas. For example, a control system may balance mass in verses available solar energy. This may provide for an endothermic reaction that consumes an amount of available energy and controls concentration and an amount of each reactant product into the chemical reactor to control the molarity and ratio of the reactants going into the reactions in order to control the products coming out of the reactions.

Some embodiments can include a synthesis reactor that may use the resultant hydrogen molecules and the carbon monoxide molecules (syngas) in the hydrocarbon fuel synthesis process. This can be catalytically reformed using known processes to produce chemicals, including liquid hydrocarbon fuels. For example, fuels such as syngas can be produced and may also be used to drive a gas turbine to produce electricity via an efficient gas turbine or it can be catalytically reformed to valuable chemicals or liquid fuels. In some embodiments, one or more tubes may be graphite reaction tube with an external SiC coating operating at up to 1500 degree C.

Figure 3:
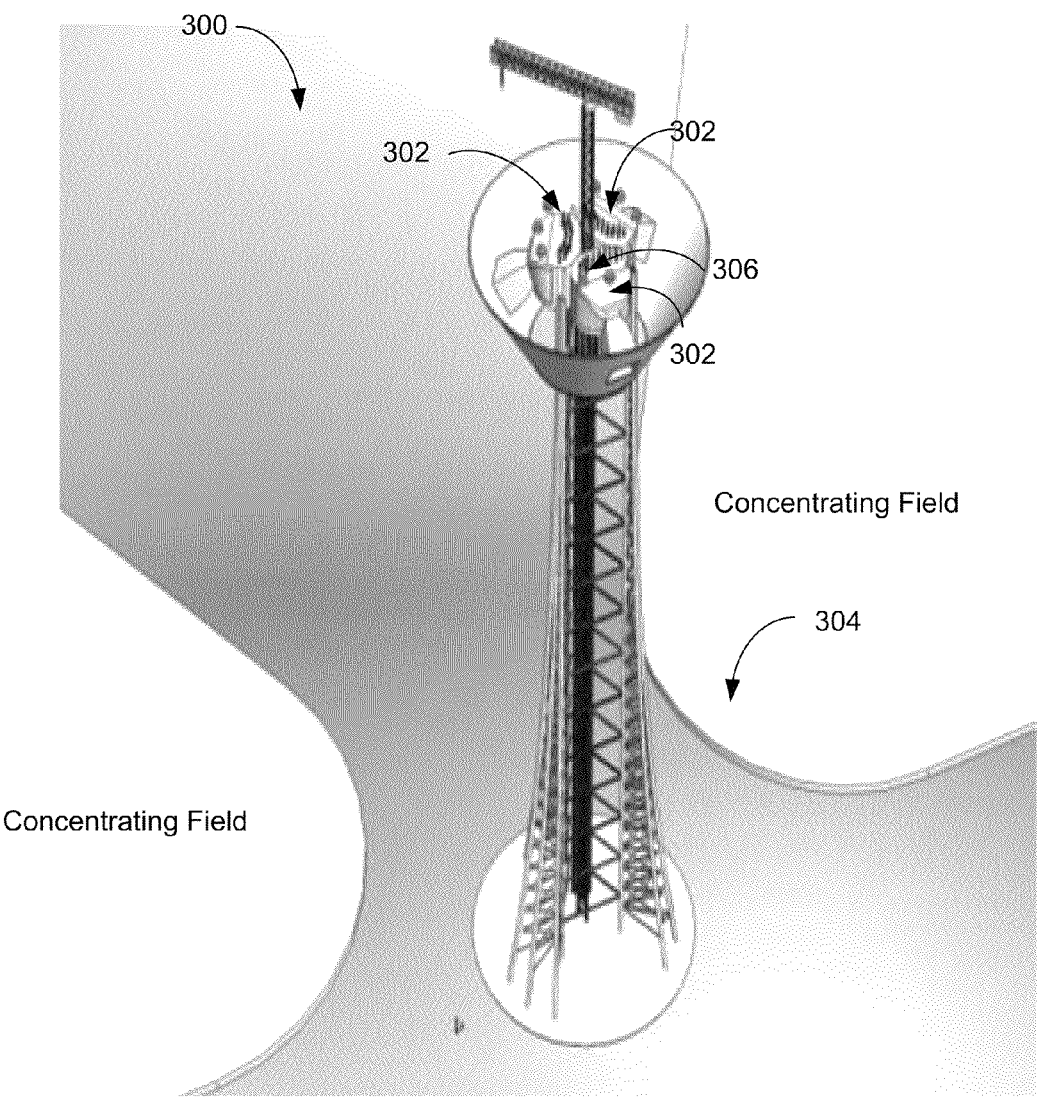
FIG. 3 illustrates a diagram of an embodiment of an example solar tower with receivers and heliostat field in accordance with the systems and methods described herein.

FIG. 3 illustrates a diagram of an example solar tower 300 with receivers 302 and heliostat field 304. In some embodiments solar tower 300 may be used to form a solar-driven bio-refinery with a pneumatic biomass feed system. The feed system can be feedstock flexible via, for example, particle size control of the biomass.

A chemical reactor 306 receives concentrated solar thermal energy from an array of heliostats 304. The chemical reactor 306 can be, for example, a multiple reactor tube, downdraft, solar driven, chemical reactor, which receives concentrated solar thermal energy from the array of heliostats 304.

A solar tower 300 may form a portion of a solar-driven bio-refinery that may also include a biomass feed system that has balancing of the feed lines to each of the reactor tubes in a multiple tube chemical reactor. For example, biomass may be fed to the solar reactor in an operation including three parts: biomass transport and preparation for feeding to the solar tower reactor, biomass transport to the top of the, e.g., 500+ foot tower, and distribution into the specific downdraft tubes of the reactor. The distribution may be performed via multiple stages.

In some embodiments, a solar-driven chemical plant can include a solar thermal receiver having a cavity with an inner wall, where the solar thermal receiver is aligned to absorb concentrated solar energy from one or more of 1) an array of heliostats, 2) solar concentrating dishes, and 3) any combination of the two. The solar driven chemical reactor can include a downdraft geometry with the multiple reactor tubes in a vertical orientation and are located inside the solar thermal receiver.

In some embodiments, the concentrated solar energy may interact with water to convert the water to steam, supply the energy for the reactant gases, and/or interact with other sources to provide heat delivery mechanisms for the heat for the gasification process of the biomass. Additionally, the solar energy may be transferred to the walls of the receiver and walls of the reactor tubes such that the heat is radiantly transferred to the biomass particles. The biomass particles have a lot of surface area to absorb the radiant heat and the particles transfer that heat to the methane molecules.

FIG. 4 illustrate results from simulations of the solar-thermal gasification of biomass with methane. Simulations were carried out for biomass gasification, with and without additive methane, to evaluate the impact of supplemental methane on the solar-thermal process.

As illustrated in FIG. 4 the reactions of an example biomass to syngas may be:

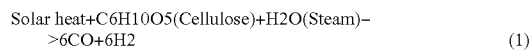

$$\text{Solar heat} + C_6H_{10}O_5\text{(Cellulose)} + H_2O\text{(Steam)} \rightarrow 6CO + 6H_2 \quad (1)$$

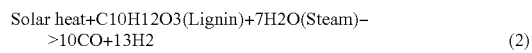

$$\text{Solar heat} + C_{10}H_{12}O_3\text{(Lignin)} + 7H_2O\text{(Steam)} \rightarrow 10CO + 13H_2 \quad (2)$$

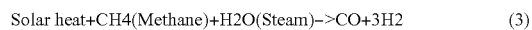

$$\text{Solar heat} + CH_4\text{(Methane)} + H_2O\text{(Steam)} \rightarrow CO + 3H_2 \quad (3)$$

Synthesis gas=nCO+mH2, where n and m variable amounts of moles.

Even if some CO2 is present in the natural gas consisting mainly of the methane above, the CO2 and CH4 react with the high heat via dry reforming to produce hydrogen and carbon monoxide.

$$CH4+CO2==>2H2+2CO \quad (4)$$

The methane addition in FIG. 4 eliminates the water gas shift reaction in reactions without methane in order to get to the desired molar H2/CO=2. Note, when operating the reforming process with concentrated solar radiation, the solar energy is converted into chemical energy and therefore, it increases the energy content of the gas.

An example biomass to syngas reaction without methane may be:

$$\text{Solar heat}+C6H10O5(\text{Cellulose})+H2O(\text{Steam})->6CO+6H2 \quad (1)$$

$$\text{Solar heat}+C10H12O3(\text{Lignin})+7H2O(\text{Steam})->10CO+13H2 \quad (2)$$

$$\text{Solar heat}+CO+H2O(\text{Steam})<-->CO2+H2 \quad (3)$$

Synthesis gas=nCO+mH2, where n and m variable amounts of moles.

Figure 5:
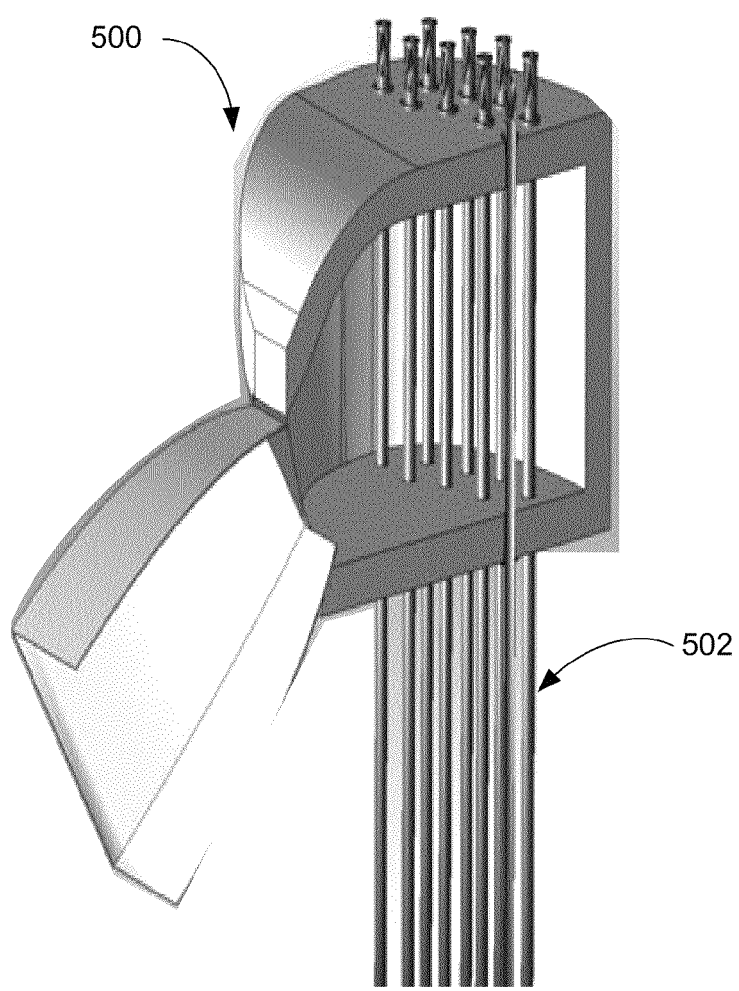
FIG. 5 illustrates a diagram of an embodiment of a solar thermal receiver with gasifier tubes in accordance with the systems and methods described herein.

FIG. 5 illustrates a diagram of a solar thermal receiver 500 with gasifier tubes 502. Solar thermal receiver 500 can form a portion of a solar-driven bio-refinery in accordance with the systems and methods described herein. The solar-driven bio-refinery can include a solar driven chemical reactor, a solar thermal receiver such as receiver 500, or both. In some embodiments, solar thermal receiver 500 can be a multiple reaction tube downdraft solar thermal receiver as well as solar driven chemical reactor. Additionally, the feed system may feed biomass particles into the multiple reaction tubes 502, in which the particles of biomass may be gasified in the presence of steam at a temperature exceeding 950 degrees C. from an exit of a gasification reaction zone of the reactor tubes.

In some embodiments, a solar-driven chemical plant may use methane from natural gas. Additionally, the biomass and natural gas may be co-fed with steam heated by the solar energy to dry reform heated CO2 with CH4 the methane with the CO2 into syngas, such that, even if some CO2 is present in the natural gas consisting mainly of methane, the CO2 and CH4 react with the high heat via dry reforming to produce hydrogen and carbon monoxide substantially free of CO2.

For example, the reaction may include:

$$\text{Energy from } H2O+CH4+CO2==>2H2+2CO+H2O.$$

In some cases, small amounts of CO2 in the natural gas can react with methane to produce additional synthesis gas. Additionally, thermodynamics indicate that a CO2-free syngas can be produced when biomass and methane are co-fed with steam at 1200 degree C. in stoichiometric proportions to produce a molar ratio of H2:CO=2 (two moles of hydrogen gas—carbon monoxide per liter). The majority of the reduction of carbon dioxide present in the generated syngas from the reactor comes from that concentrated solar energy, which can externally drive the steam reforming of the methane and biomass gasification of the carbon in the biomass reactions. Additional CO2 reduction may occur by rapid quenching of the reactor products to avoid the water gas shift reaction and a dry reforming of methane reaction simultaneous with the steam reforming to consume CO2 present and/or generated during the reactions in the reactor tubes. Also the 2:1 H2:CO molar ratio can be in a range from 2.0 to 2.8.

In some examples, when natural gas is used, it is possible for the plant to produce 5 to 10% of the syngas on demand via oxidation of NG using high temperature oxidizers (O2, not air) that essentially fits into a tee (T) just before the downstream syngas catalytic reforming synthesis. Thus, in a partial oxidation system, the system can have a catalytic oxidizer. A reaction that may take place is: CH4+0.5O2=CO+2H2 (partial oxidation reforming). Additionally, this supplemental source may be used to raise the amount of H2 present in H2:CO syngas. This process may be run in parallel with the main solar driven reactor.

In some examples, the co-feeding of methane, potentially in natural gas, with water and biomass, produces a CO2-free synthesis gas. In such an example CO2 levels may be less than 7% (by volume) of the syngas stream and have a desirable molar ratio of H2:CO=2. Such a reaction may also avoid a water-gas-shift reaction that may otherwise produce CO2. Tar formation may also be avoided at an approximately 1100-1300 degree C. operating temperature. In some examples, use of biomass carbon can produce CO2-free syngas. Substantially 100% of the biomass carbon may produce the useful CO component of syngas. Additionally, with CO2 levels at less than 7% (by volume) of the syngas stream, a downstream amine train to remove CO2 prior to catalytic reforming of the syngas might no longer be necessary. Operation in temperature regimes where tar may be eliminated and reaction can be extremely fast due to radiation heat transfer may be used.

In some embodiments, co-feeding of methane (CH4) with the biomass may be used such that particles of biomass facilitate the radiation heat transfer. This can raise the temperature in the tubes to a level to reform the methane and cause the biomass gasification reaction. In other systems, separate streams mighty be required and a separate solid particle addition might be needed to accomplish this such that the conversion of methane is combined with biomass gasification using steam heated by the solar energy to generate the synthesis gas.

In some embodiments, a solar-driven reactor may be located inside a receiver. A receiver is a cavity that transforms solar radiant energy into thermal energy. The receiver can comprise multiple reactor tubes. The reactor tubes may allow methane or natural gas and steam to pass through a fluidized bed of inert particles to cause a steam methane reaction. Natural gas can be passed through a stream such that a methane reaction occurs with a dry reforming of methane with CO2 occurs. Additionally, multiple reactors can be incorporated in a receiver. To increase the size of a plant, more receivers may be added. Each reactor may be a downdraft tube.

Figure 6:
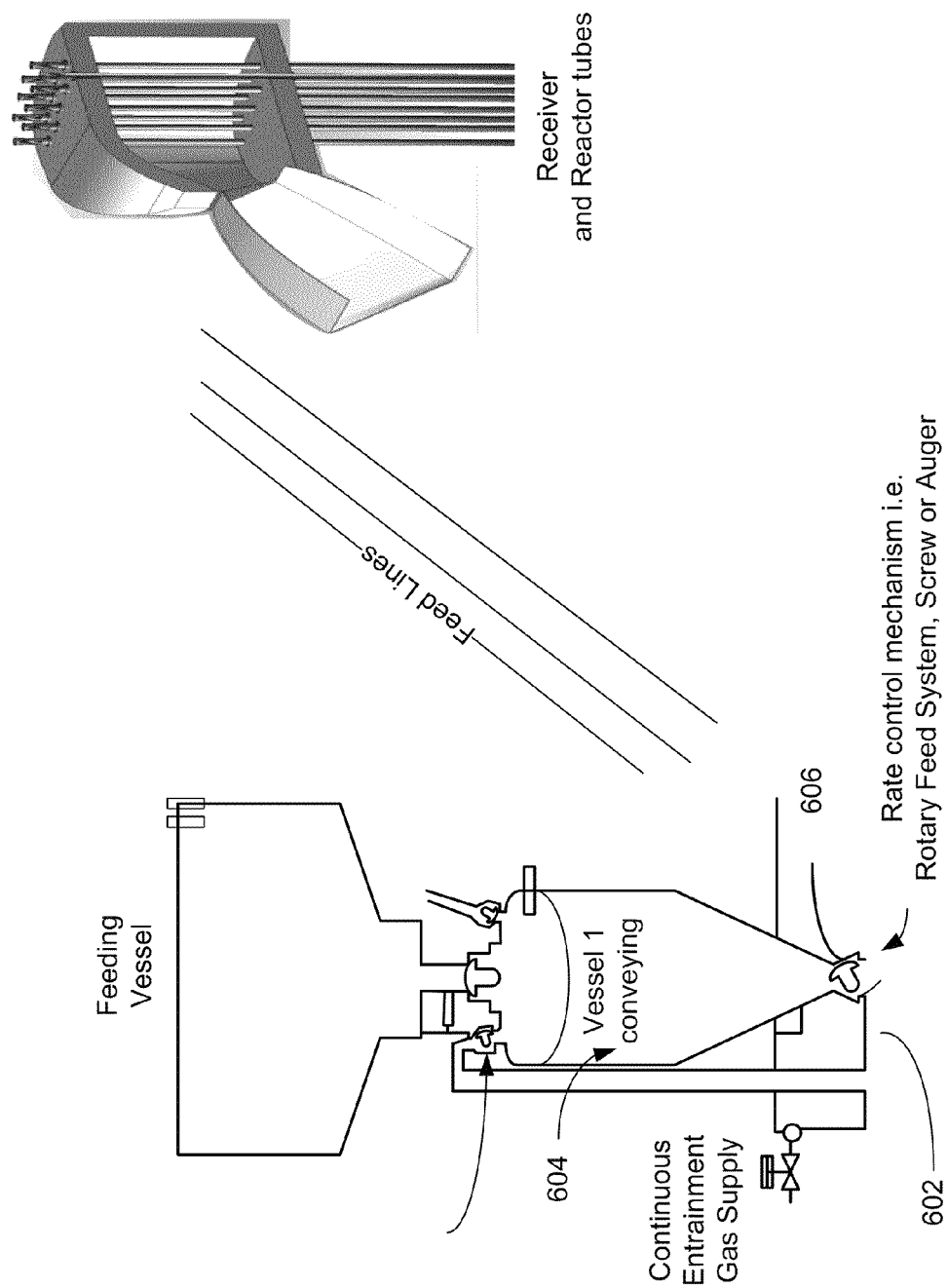
FIG. 6 illustrates a block diagram of an embodiment of a feed system in accordance with the systems and methods described herein.

FIG. 6 illustrates a block diagram of a feed system 600. The grinding system 603 has a mechanical cutting device used to grind the biomass into primary particles, which are to be fed into the solar driven chemical reactor. The grinding system supplies primary particles that have an average smallest dimension size between 200 microns (um) and 2000 um, with a general range of between 500 um and 1000 um to a lock hopper system 604 with a standard belt conveyer. The biomass particles are then fed across a pressure boundary into a pressurized entrainment gas for feeding into in the solar driven chemical reactor. The feeding vessel may use an Auger/Screw feeder or an airlock-type rotational solids feeding/rate metering device.

The entrainment-flow biomass feed system 600 can include a pressurized lock hopper 604 that feeds the biomass to a rotating screw conveyor 602 and a metering device and then into an entrainment gas pipe at the lock hopper exit 606. A flow splitter distributes the particles of biomass into multiple entrainment gas lines to feed at least two or more of the multiple reactor tubes making up the solar driven chemical reactor. The entrainment gas for the pneumatic biomass feed system may be a pressurized dry steam generated from waste heat recovered from either 1) the methanol/Methanol-To-Gasoline (MTG) units in the hydrocarbon fuel synthesis process or 2) the products from the gasification reaction in the solar driven chemical reactor. The entrainment gas may also be CO2, natural gas, an inert gas, steam generated in any fashion, or other similar entrainment gas.

Additionally, an entrained-flow biomass feed system having one or more feed lines to feed the biomass particles into the multiple reactor tubes, in which a separate entrainment line and metering device of the entrained-flow biomass feed system is used for each of the gasifier reactor tubes in the chemical reactor. This may allow for balancing of 1) amount of particles of biomass flowing through the feed line to each reactor tube to 2) an amount of solar energy available for that reactor tube in the multiple tube solar driven chemical reactor. Feed rate of the biomass particles can be controlled by a metering device and controlling a rotational rate of a screw 602 at a base of the lock hopper 604, which responds to a feed demand signal received from the control system.

Thus, control of the rotational rate of the screw or auger 602 can move set amounts of biomass along the axis of rotation of the auger 602. The auger 602 may be located at the base of the lock hopper 604 and can be controlled by a control system to respond to feed demand of the system. As discussed, the control system controls the feed rate of particles of biomass in the solar driven chemical reactor based on an amount of solar energy available indicated by sensors including temperature sensors and/or light meters.

In some embodiments, additional biomass may be used in a biomass methane gasification reformation as compared to biomass gasification. For example, in some embodiments (about 2.5×) to produce a given mass of the required H2/CO=2 molar ratio. In this example embodiment, the reaction is substituting carbon in the natural gas for carbon sourced from the biomass carbon. In addition, there may be excess water in the reactor for the straight biomass gasification route. Hence, reactor materials may be oxidation resistant and steam resistant.

Some embodiments include an entraining gas biomass feed system that uses an entrainment carrier gas comprising natural gas, steam, oxygen, air, and/or any combination of these and supplies a variety of feed stock biomass sources fed as particles into the solar driven chemical reactor. The entrainment carrier gas can be natural gas, steam, or any combination of natural gas and steam. Additionally, the entraining gas biomass feed system may receive ground and pulverized biomass with a particle size that is between 150 and 300 microns. The particle size has an average smallest dimension size between 200 microns um and 2000 um in diameter, such to fit through the holes in the filters, with a general range of between 500 um and 1000 um. Similar particle size, and use of the multiple tube design with the external concentrated solar thermal energy driving the biomass gasification reaction, steam reforming reaction, and dry reforming reaction may be used to allow the process to be feedstock flexible, with no major equipment redesign required to change feedstocks.

In some embodiments, two or more types of biomass may be fed. These biomasses may be fed individually or in combinational mixtures, from the group consisting of cellulose, lignin, pine sawdust, rice straw, corn stover, switch grass, energy crops, source separated green wastes, sorghum, Algae, and other similar biomass sources. This may be done as long as a few parameters are controlled, such as particle size of the stock biomass and operating temperature range of the reactor tubes.

Figure 7:
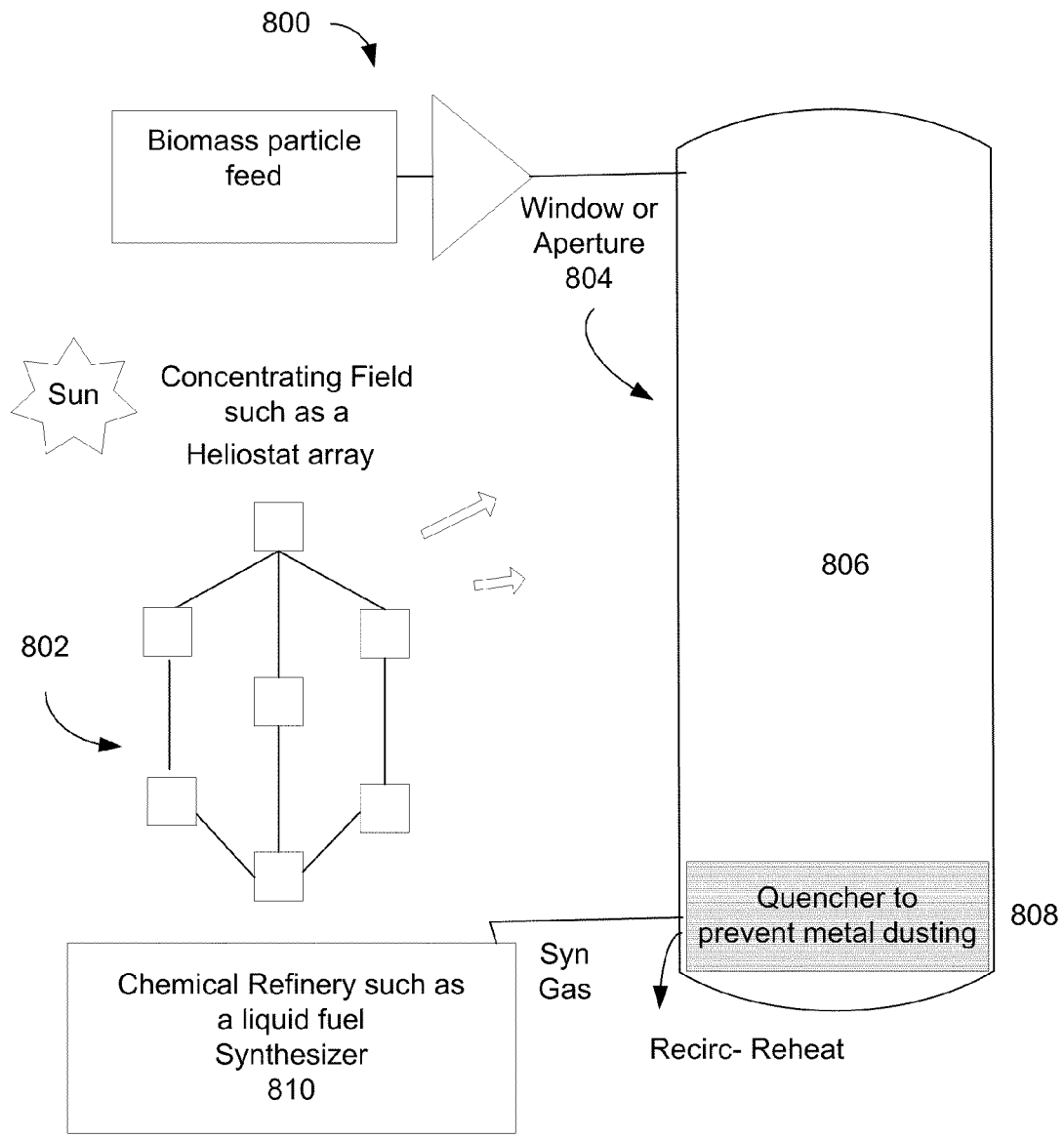
FIG. 7 illustrates a diagram of an embodiment of a solar-driven bio-refinery in accordance with the systems and methods described herein.

FIG. 7 illustrates a diagram of a solar-driven bio-refinery 700 in accordance with the systems and methods described herein. An array of heliostats 702 can be used to focus light onto a window 704 of a reactor 706. In reactor 706 biomass particles can be reduced to syngas, which in turn can be synthesized into liquid fuel in liquid fuel synthesizer 708.

For example, in some embodiments, an on-site fuel synthesis reactor 708 may receive the hydrogen and carbon monoxide products from the gasification reaction and use the hydrogen and carbon monoxide products in a hydrocarbon fuel synthesis process to create a liquid hydrocarbon fuel. The fuel synthesis reactor 706 may be geographically located on the same site as the chemical reactor and integrated into the process to utilize the hydrogen and carbon monoxide products from the gasification reaction.

In some embodiments, the addition of methane (CH4 i.e. primary constituent in natural gas) can be used at the solar-thermal operating temperatures to stretch the use of biomass carbon to produce essentially CO2-free sygnas (at less than CO2 levels at less than 7% (by volume) of the syngas stream) via dry reforming of methane with the carbon dioxide. The biomass and the supplemental natural gas are rapidly gasified and reformed with steam, and all are heated by the solar energy concentrated into the solar-thermal gasifier, which primarily uses radiant heat to drive the chemical reaction.

In some embodiments, an on-site chemical plant that is geographically located on the same site as the chemical reactor and integrated to receive the hydrogen and carbon monoxide products from the gasification reaction may be used. The on-site chemical plant can have an input to receive the hydrogen and carbon monoxide products and use them in a hydrocarbon fuel synthesis process to create a liquid hydrocarbon fuel, or other chemical product.

Additionally, down stream of the reactor, one or more knock out drums may exist to remove excess water from the generated syngas. For biomass/methane, less than an amount of 2-5% of CO2 is formed.

Figure 8:
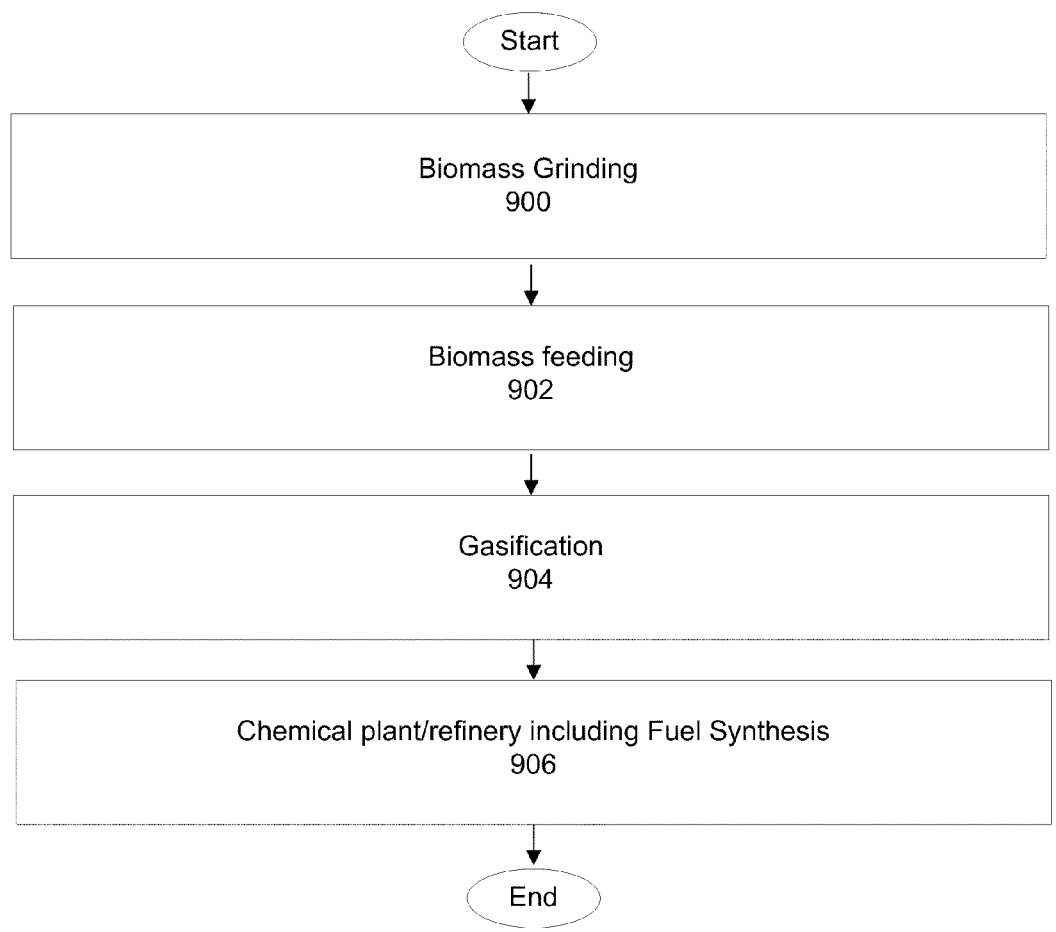
FIG. 8 illustrates a flow diagram of an embodiment of the systems and methods described herein.

FIG. 8 illustrates a flow diagram in accordance with the systems and methods described herein. In step 800, biomass grinding can occur. Equipment generally used for grinding biomass includes impact mills (e.g. hammer mills), attrition mills, and kinetic disintegration mills (e.g. flail mills). A hammer mill system can be used to grind the bales (loaded by conveyer) into primary particles, which are to be fed into the solar thermal gasifier. The re-ground particles have an average size between 500 um and 1000 um, and are loaded into the lock hopper system with a standard belt conveyer.

In step 802 biomass feeding occurs. In some embodiments, high pressure feeding may be used. High pressure feeding of solids of biomass with gasification at pressure may reduce capital cost due to the ability to use smaller compressors in some such systems. Additionally, operating cost may be reduced because energy for pressurizing carrier gas comes from the sun, as opposed to from electricity. The lock hopper system can feed the reactor processes at pressure. For example, the feeding system can entrain the biomass materials in steam at high pressure, successfully disengage the particulates in the cyclone system, and distribute flow appropriately to the reactor tubes.

In step 804, gasification occurs. For example, in some embodiments, concentrated solar thermal energy drives gasification of the particles of the stock biomass to generate at least hydrogen and carbon monoxide products from the gasification reaction.

In step 806 fuel synthesis occurs. An on-site fuel synthesis reactor can receive the hydrogen and carbon monoxide products from the gasification reaction and use the hydrogen and carbon monoxide products in a hydrocarbon fuel synthesis process to create a liquid hydrocarbon fuel. The fuel synthesis reactor may be geographically located on the same site as the chemical reactor and integrated into the process to utilize the hydrogen and carbon monoxide products from the gasification reaction.

We claim:

1. A chemical reactor driven by radiant heat with an exit temperature of product gases greater than 900 degrees C., comprising:
a radiant heat-driven chemical reactor having multiple reactor tubes located inside a cavity of a thermal receiver configured to gasify particles of biomass in a presence of steam ($H_2O$) to produce a low $CO_2$ synthesis gas that includes hydrogen, carbon monoxide gas, and less than 7% $CO_2$ by total volume generated in a gasification reaction of the particles of biomass using thermal energy from the radiant heat, where the chemical reactor is in fluid communication with a source of the steam, wherein the multiple reactor tubes and the thermal receiver are configured to cooperate such that heat is radiantly transferred to the particles of biomass in order to provide enough energy required for the gasification reaction of the particles of biomass to drive the gasification reaction primarily with radiant heat to produce the low $CO_2$ synthesis gas;
a steam reformer in fluid communication with a source of methane-based gas, where the steam reformer is configured to produce reformate that includes hydrogen and carbon monoxide gas;
a mixer in fluid communication with the chemical reactor and steam reformer that is configured for mixing of the reformate and biomass gasification products to produce a combined low $CO_2$ synthesis gas having a molar $H_2:CO$ ratio of between 2.0-3.0, as well as eliminates any need for a component downstream of the chemical reactor to perform a water-gas-shift reaction;
an on-site fuel synthesis reactor in fluid communication with an outlet of the mixer;
a lock hopper containing the particles of biomass; and
a splitting device configured to supply the particles of biomass from the lock hopper to two or more feed lines in an entrained-flow biomass feed system, wherein the entrained-flow biomass feed system is configured to use an entrainment carrier gas to move the particles of biomass into the radiant heat driven chemical reactor, where the two or more feed lines are configured to supply the particles of biomass having an average smallest dimension the particles of equal to or less than 2000 um to the chemical reactor.

2. The chemical reactor of claim 1, wherein the thermal receiver has cavity walls and is aligned to absorb energy from a heat source.

3. The chemical reactor of claim 2, where the radiant heat-driven chemical reactor is configured for the particles of biomass to be gasified simultaneously with the methane-based gas undergoing steam reformation in the same chemical reactor, wherein the steam reacts with both the particles of biomass and the methane-based gas, but the biomass and methane-based gas do not react with each other, and wherein a steam ($H_2O$) to carbon molar ratio is in a range of 1:1 to 1:4, wherein the radiant heat-driven chemical reactor has a downdraft geometry with the multiple reactor tubes in a vertical orientation that are located inside the thermal receiver, and wherein the chemical reactor is configured to convert carbonaceous biomass materials into the carbon monoxide and hydrogen by reacting the particles of biomass with the steam in a biomass gasification reaction and the steam with the methane-based gas at high temperatures, 700-1500 degrees C., which then results in the combined low $CO_2$ synthesis gas.

4. The chemical reactor of claim 2,
where the thermal receiver is configured to gasify the particles of biomass simultaneously with the methane undergoing steam reformation in the same chemical reactor, wherein the methane comes from natural gas, and the particles of biomass and the natural gas are co-fed with heated steam to dry reform the methane with $CO_2$ either contained within the natural gas or fed as a separate feedstock, such that even if some $CO_2$ is present in the natural gas, consisting mainly of methane, the $CO_2$ and $CH_4$ react using a high heat of 750-1300 degrees C. via dry reforming to produce the hydrogen and carbon monoxide, and
wherein the particles of biomass and the methane are co-fed with the steam at the temperature ranges of 750-1300 degrees C. in stoichiometric proportions to produce a molar ratio of $H_2:CO$ in a range from 1.0 to 3.0.

5. The chemical reactor of claim 1, wherein the thermal receiver is configured to support a steam reforming process at a temperature of 700-1500 degrees C. such that the water-gas-shift reaction that is equilibrium favored at lower temperatures is avoided, and thus prevents extra $CO_2$ creation from the water-gas-shift reaction, where the steam reformer is configured to perform the reaction using the methane-based gas with a steam reforming reaction which allows the gasification reaction in the chemical reactor to generate a desired molar ratio for liquid fuels and chemical synthesis without the water-gas-shift reaction.

6. The chemical reactor of claim 1, wherein the multiple reactor tubes and thermal receiver are configured to cooperate such that heat is radiantly transferred to the particles of biomass in order for a combination of i) the particles of biomass having the average smallest dimension of equal to or less than 2000 um to the chemical reactor, ii) an operating temperature of the chemical reactor greater than 1100 degrees C. supplied by a heat source, and iii) the thermal energy primarily being driven by the radiant heat to produce the low $CO_2$ synthesis gas at an outlet of the chemical reaction having a substantial tar destruction to less than below 50 mg/m^3 in the reaction products that include the hydrogen and carbon monoxide gas, wherein tar formation is mitigated at an approximately 1100-1300 degrees C. operating temperature.

7. The chemical reactor of claim 1,
wherein the multiple reactor tubes are made of materials that are oxidation resistant and steam resistant; and
wherein the reformate has a 3:1 $H_2:CO$ ratio and the biomass gasification products have a 1:1 $H_2:CO$ ratio, so less biomass is needed to achieve a syngas product with an approximate 2.1-2.8:1 $H_2:CO$ ratio that is appropriate for liquid fuels and chemical synthesis than if the particles of biomass were gasified without the methane-based gas.

8. The chemical reactor of claim 4, wherein within the multiple reactor tubes the methane-based gas is co-fed with the particles of biomass such that the particles of biomass facilitate a radiation heat transfer to raise a temperature in the multiple reactor tubes to a level to reform the methane and cause a biomass gasification reaction such that the steam reforming of the methane and the dry reforming of the methane is combined with the biomass gasification reaction; and wherein the energy from a heat source is transferred to walls of the thermal receiver and walls of the multiple reactor tubes such that heat is radiantly transferred to the particles of biomass, and then the particles of biomass transfer the heat effectively to the methane and steam molecules.

9. The chemical reactor of claim 1,
wherein the entrained-flow biomass feed system is configured to use the entrainment carrier gas comprising natural gas, steam, air, and/or any combination of these and to supply a variety of sources of biomass feedstock fed as particles into the radiant heat-driven chemical reactor;
wherein the particle size distribution of the biomass feedstock has a general range of between 500 um and 1000 um; and a use of a simple multiple reactor tube design with radiant heat driving the biomass gasification reaction allows the process to be feedstock flexible, with no major equipment redesign required to change feedstocks; and
wherein the variety of sources includes two or more types of biomass that can be fed, individually or in combinational mixtures, from the group consisting of cellulose, lignin, forestry wastes and forestry thinnings, by controlling particle size of the stock biomass feedstock and operating temperature range of the multiple reactor tubes.

10. The chemical reactor of claim 2, further comprising:
a control system configured to control the thermal receiver temperature by factoring a biomass feed rate against available energy from the heat source such that the temperature in the thermal receiver is maintained at a desired setpoint in the range of 800-1600 degrees C. by a balance of energy consumed by the gasification reaction and reactant/product sensible heat, and thermal losses from the thermal receiver by radiation, convection and/or conduction; and
wherein the control system 1) keeps the temperature high enough (1000-1300 degrees C. in the chemical reactor) for a substantially entire conversion of the particles of biomass to product gases and an elimination of tar products to a concentration of less than 200 mg/m^3, and 2) keeps the temperature in the chemical reactor low enough (<1600 degrees C.) for walls of the multiple reactor tubes to not structurally weaken or significantly reduce thermal receiver efficiency.

11. The chemical reactor of claim 1, wherein the on-site fuel synthesis fuel reactor has a supply input to receive the combined low CO2 syngas containing the hydrogen molecules and carbon monoxide molecules from the radiant heat-driven chemical reactor, where the on-site fuel synthesis fuel reactor is configured to use the syngas in a hydrocarbon fuel synthesis process which is catalytically reformed to produce chemicals.

12. A radiant heat-driven reactor located inside a receiver, comprising:
a cavity that transforms radiant energy into thermal energy, where the receiver encloses multiple reactor tubes of the radiant heat-driven reactor, and the reactor tubes are configured for reactant gases consisting of 1) methane, 2) natural gas, 3) steam, or 4) any combination of the three to pass through a heat transfer aid configured to cause a steam methane reaction using the thermal energy from the radiant energy;
wherein the heat transfer aid is configured to heat the reactant gases, where the heat transfer aid is one or more of the following located inside each reactor tube: a fluidized bed of inert particles, a reticulate porous ceramic (RPC) foam, a ceramic monolith, ceramic tubes or aerogels, open structured packed rings including Raschig rings, gauze or wire constructed of a high temperature-resistant material, and any combination of these; and
wherein radiation is a primary mode of heat transfer to the heat transfer aids from the walls of the reactor tubes, and conduction, convection, or some combination of the two is a secondary mode of heat transfer.

13. The radiant heat-driven reactor of claim 12, further comprising:
a moving bed of carbonaceous feedstock through which a gasification agent flows in a co-current or counter-current configuration to achieve gasification and the moving bed is heated with the thermal energy.

14. The radiant heat-driven reactor of claim 12, further comprising:
a source of the methane in fluid communication with the radiant heat-driven reactor;
a source of biomass in fluid communication with the radiant heat-driven reactor; and
a first reactor tube that is a graphite reaction tube with an external SiC coating configured to operate at up to 1500 degrees C., wherein the radiant heat-driven reactor is configured to add the methane to the biomass such that the energy requirement of the radiant heat-driven reactor to produce an equivalent amount of syngas is lower, and the biomass is gasified at a high enough temperature using a heated transport tube reactor, such that tar formation is substantially reduced to less than 200 mg/m^3.

15. The radiant heat-driven reactor of claim 12, further comprising:
a source of the natural gas in fluid communication with the radiant heat-driven reactor; and
one or more high temperature oxidizers configured to oxidize the natural gas such that the radiant heat-driven reactor produces 5% to 10% of a high H2syngas (>2:1 H2:CO ratio) on demand that is combined with syngas from a biomass gasification reaction such that the high H2 syngas is used to raise an amount of H2 present in the combined syngas to a desired H2:CO ratio.

* * * * *